(12) United States Patent
Vorozhtsov et al.

(10) Patent No.: US 7,335,376 B2
(45) Date of Patent: Feb. 26, 2008

(54) METHOD FOR PHOTODYNAMIC THERAPY AND APPLICATOR FOR CARRYING OUT SAID THERAPY

(75) Inventors: Georgy Nikolaevich Vorozhtsov, Moscow (RU); Anatoly Borisovich Davydov, Moscow (RU); Sergei Georgievich Kuzmin, Dolgoprudny Moskovskoi oblasti (RU); Viktor Borisovich Loschenov, Moscow (RU); Yury Mikhailovich Luzhkov, Moscow (RU); Evgeny Antonovich Lukyanets, Moscow (RU); Gennady Alexandrovich Meerovich, Korolev Moskovskoi obl. (RU); Gennady Lvovich Khromov, Moscow (RU)

(73) Assignee: Federalnoe Gosudarstvennoe Unitarnoe Predpriyatie "Gosudarstvenny Nauchny Tsentr Nauchno-Issledovatelsky Institut Organicheskikh Poluproduktov I Krasitelei" (FGUP "GNTTS NIOPIK"), Moscow (RU)

( * ) Notice: Subject to any disclaimer, the term of this patent is extended or adjusted under 35 U.S.C. 154(b) by 385 days.

(21) Appl. No.: 10/332,476

(22) PCT Filed: Jan. 11, 2002

(86) PCT No.: PCT/RU02/00004

§ 371 (c)(1),
(2), (4) Date: Jan. 8, 2003

(87) PCT Pub. No.: WO02/054933

PCT Pub. Date: Jul. 18, 2002

(65) Prior Publication Data

US 2003/0195250 A1    Oct. 16, 2003

(30) Foreign Application Priority Data

Jan. 12, 2001  (RU) ............... 2001100688

(51) Int. Cl.
*A61F 13/00* (2006.01)
*A61F 15/00* (2006.01)
*A61K 9/70* (2006.01)
*A61L 15/16* (2006.01)
*A61L 15/00* (2006.01)

(52) U.S. Cl. .......... 424/443; 424/444; 424/445; 602/50; 602/54; 602/56

(58) Field of Classification Search ........ 424/443–445, 424/446, 447, 448, 449; 427/2.31; 602/50, 602/54, 48, 58; 604/2, 304, 305, 306, 307, 604/308

See application file for complete search history.

(56) References Cited

U.S. PATENT DOCUMENTS 3,425,412 A * 2/1969 Pope ..................... 602/59

(Continued)

FOREIGN PATENT DOCUMENTS

SU     2053813     2/1996

(Continued)

OTHER PUBLICATIONS

Ormrod, D. et al., "Topical Aminolevulinic Acid HCI Photodynamic Therapy", Am J Clin Dermatol Mar.-Apr. 2000; 1 (2): 133-9.

(Continued)

*Primary Examiner*—San-Ming Hui
(74) *Attorney, Agent, or Firm*—Winstead PC

(57) ABSTRACT

The present invention relates to medicine, more concretely to photodynamic therapy, and may be used in oncology and dermatology.

A method is proposed for photodynamic therapy of pathological surface formations, which comprises sensitizing a surface of the pathological area by superposing an applicator containing 5-aminolevulinic acid, and irradiating the sensitized area with therapeutic optical radiation in the spectral range of 625-700 nm, wherewith an applicator is used which is transparent in the spectral range of at least 625-700 nm, and irradiation is carried out through the applicator.

Wherewith therapeutic irradiation is carried out under control of the intensity of fluorescence of the tissues of the pathological area by irradiation of the tissues in the spectral range of 625-635 nm and measurement of the intensity of fluorescence in the range of 635-700 nm through the applicator.

In the method an applicator may be used which is also transparent in at least one of the spectral ranges 390-460 nm, 510-540 nm or 570-590 nm. The applicator used in the proposed method consists of a base of a bioinertial material and a sensitizing layer including a carrier and 5-aminolevulinic acid dissolved or dispersed in the carrier. The base is made in the form of a film of a bioinertial polymer, transparent in the spectral range of at least 625-700 nm, and the carrier is made in the form of a film layer of biocompatible hydrophilic terpolymers of N-vinylpyrrolidone, amide of acrylic acid and of ethyl ether of acrylic acid with a ratio of the monomeric links respectively (20-35):(35-60):(20-30) wt. % and a molecular weight of from 20 000 to 1 000 000 Daltons.

The bioinertial polymer may also be transparent in at least one of the spectral ranges of 390-460 nm, 510-540 nm or 570-590 nm. This polymer is regenerated cellulose, polyethylene terephthalate or a polyamide.

The proposed method for photodynamic therapy and the applicator for implementation of the method make it possible to enhance the efficacy of photodynamic therapy and reduce the expenditure of 5-aminolevulinic acid.

5 Claims, No Drawings

U.S. PATENT DOCUMENTS

| | | | |
|---|---|---|---|
| 5,079,262 A * | 1/1992 | Kennedy et al. | 514/561 |
| 5,489,279 A * | 2/1996 | Meserol | 604/290 |
| 6,262,144 B1 * | 7/2001 | Zhao et al. | 523/201 |

FOREIGN PATENT DOCUMENTS

| | | |
|---|---|---|
| SU | 2123326 | 12/1998 |
| SU | 2145247 | 2/2000 |
| SU | 2146159 | 3/2000 |
| WO | WO 95/05813 | 3/1995 |
| WO | WO 95/07077 | 3/1995 |

OTHER PUBLICATIONS

Hillemanns, P. et al., "Photodynamic therapy in women with cervical intraepithelial neoplasia using topically applied 5-aminolevulinic acid", Int J Cancer Mar. 31, 1999; 81 (1):34-8.

XVII Conference on High Molecular Compounds. Kazan, Jul. 2-6, 1973. Publisher "Nauka", Moscow 1973. (Russian, with English translation).

* cited by examiner

METHOD FOR PHOTODYNAMIC THERAPY AND APPLICATOR FOR CARRYING OUT SAID THERAPY

FIELD OF THE INVENTION

The present invention relates to medicine, more concretely to photodynamic therapy (PDT), and may be used in oncology and dermatology.

BACKGROUND OF THE INVENTION

A method is known for photodynamic therapy of pathological surface areas, comprising applicative sensitization of the surface of the pathological area by superposing an applicator on the base of a layer of liquid ointment comprising 5-aminolevulinic acid (5-ALA), with an optically opaque coating on top of that layer, removing the layer of ointment after a predetermined time, carrying out a laser-fluorescent check of the concentration of a sensitizer (derivatives of porphyrin) in the tissues of the pathological area, and carrying out irradiation of that area with optical radiation in the spectral range of 625-700 nm [publication—PCT application WO 95/07077, published 16 Mar. 1995, IPC A 61 K 31/195]/1/.

The known applicator described in /1/ comprises a carrier in the form of an ointment having a fluid, gel-like suspension or emulsion form, and 5-ALA dissolved or dispersed in the carrier.

Drawbacks of the known method for PDT and the known applicator /1/ are the absence of the possibility of carrying out therapeutic irradiation of the surface of the pathological area and control of the accumulation of the sensitizer in its tissues during the process of sensitization, the complexity of precise dosage of 5-ALA over the surface of the pathological area, a large non-productive expenditure of 5-ALA because of the necessity to remove the ointment prior to irradiation, the possibility for the accidental removal of the ointment, especially when substantial pathological formations in need of sensitization are positioned on areas of a patient's body which are hidden by clothes. All of these reduce the therapeutic efficacy of PDT.

The drawbacks of the method for photodynamic therapy of the pathological surface areas and the applicator, taught in /1/, which are related to the possibility for the accidental removal of the ointment and the complexity of precise dosage of the 5-ALA over the surface of the area and are due to the consistency of the ointment, are partially removed in the method for dynamic therapy of pathological surfaces of areas and in the applicator that are taught in the PCT publication of application WO 95/05813, published Mar. 2, 1995 [IPC A 61 K 31/195]/2/. These are the analogues most similar to the proposed invention. The applicator taught in /2/ contains a base of bioinert material and a sensitizing layer including a polymer carrier and 5-ALA dissolved or dispersed in the carrier. The applicator of /2/ is optically opaque, since metal foil, polyester, rubber sponge, frothed polymers or other materials, which are not transparent in respect to optical radiation (for which they are absorbers or dispersals), are used as the base of bioinert material therein. This does not make it possible in the known method to carry out either therapeutic irradiation of the surface of the pathological area or a fluorescent check of the concentration of the sensitizer in the process of sensitization, since these operations are only carried out with the applicator removed. All this, as in /1/, reduces the therapeutic efficacy of PDT.

SUMMARY OF THE INVENTION

The object of enhancing the efficacy of photodynamic therapy of pathological surface areas with the use of an applicator on the base of 5-aminolevulinic acid for sensitization is achieved in the invention by optimization of the processes of sensitization and irradiation of the pathological area, and also reduction of the expenditure of 5-aminolevulinic acid.

DISCLOSURE OF THE INVENTION

The object of the invention is achieved in that in a method for photodynamic therapy of pathological surface formations, which comprises sensitizing a surface of the pathological area by superposing an applicator containing 5-aminolevulinic acid, and irradiating the sensitized area with therapeutic optical radiation in the spectral range of 625-700 nm, an applicator is used which is transparent in the spectral range of at least 625-700 nm, and irradiation is carried out through the applicator.

The object is also achieved in that the therapeutic irradiation may be carried out under control of the intensity of fluorescence of the tissues of the pathological area, wherewith the tissues are irradiated in the spectral range of 625-635 nm and the intensity of fluorescence is measured in the range of 635-700 nm through the aforesaid applicator.

The object is also achieved in that an applicator is used which is also transparent in at least one of the spectral ranges 390-460 nm, 510-540 nm or 570-590 nm, while monitoring the intensity of fluorescence of the tissues of the pathological area is carried out during irradiation in one of the aforesaid ranges and measurement of the intensity of fluorescence in the range of 635-700 nm through the aforesaid applicator. The stated object is achieved in that in an applicator comprising a base of a bioinert material and a sensitizing layer including a carrier and 5-aminolevulinic acid dissolved or dispersed in the carrier, the base is made in the form of a film of a bioinert polymer, transparent in the spectral range of at least 625-700 nm, and the carrier is a film layer of biocompatible hydrophilic copolymers of N-vinylpyrrolidone with derivatives of acrylic acid, which copolymers are terpolymers of N-vinylpyrrolidone, acrylic acid amide, and ethyl ester of acrylic acid with a ratio of the monomeric links respectively (20-35):(35-60):(20-30) wt. % and a molecular weight of from 20 000 to 1 000 000 Daltons.

Furthermore, the bioinert polymer may also be transparent in at least one of the spectral ranges of 390-460 nm, 510-540 nm or 570-590 nm.

Regenerated cellulose, polyethylene terephthalate or a polyamide may be used as the bioinert polymer.

The proposed method is carried out in the following manner.

An applicator in the form of a film corresponding in respect to shape and size to the topology of the area presumed for sensibilization in accordance with the chosen method for treatment is superposed on the surface of the pathological area. The applicator consists of a base in the form of a film of a bioinert polymer, transparent in the spectral range of at least 625-700 nm (for example, from regenerated cellulose, polyethylene terephthalate or polyamide), and a sensitizing layer comprising a biocompatible hydrophilic polymer, which is a copolymer of N-vinylpyrrolidone with derivatives of acrylic acid and 5-ALA dissolved or dispersed therein. The applicator is laid on the surface of the pathological area and further it is held on that surface by adhesion. After some time, for example, after 2-3 hours, the concentration of the sensitizer (derivatives of porphyrin) on the sensitized area is controlled by irradiating it through the film by optical radiation in one of the spectral ranges 390-460 nm, 510-540 nm, 570-590 nm or 625-635 nm and measuring the intensity of fluorescence of the derivatives of porphyrin in the spectral range of 635-700 nm. If in accordance with these measurements, the concentration of the sensitizer corresponds to the therapeutic level, selected in accordance with the method for treatment, or exceeds it, the sensitized areas are irradiated through the film by therapeutic optical radiation in the spectral range of 625-700 nm. If, however, the concentration of the sensitizer in the tissues is not sufficient, further sensitization is continued with monitoring (periodically or continuously) until the necessary value of the concentration of the sensitizer is reached, after which therapeutic irradiation is carried out.

Biocompatible hydrophilic polymers are prepared by the joint polymerization of N-vinylpyrrolidone, acrylic acid amide, and ethyl ester of acrylic acid [Davidov O. B., Khromov G. L. "Joint polymerization of vinyl heterocyclic monomers and derivatives of acrylic acid in the preparation of biosoluble polymers." Papers of XVIII All-Union Conference on High-Molecular Compounds, p. 19, Kazan, 1973]. In order to obtain a polymer of the required molecular weight, polymerization is carried out in a solution or in a "solvent-precipitator" system. By varying the weight ratios of the monomers and taking the constant of their copolymerization into account, biocompatible polymers are obtained with a different hydrophilic-hydrophobic balance of the monomer links in the macromolecule.

EXAMPLES OF CONCRETE REALIZATION OF THE METHOD

Example 1

In order to carry out sensitization of a pathological area with basal cell skin carcinoma having a thickness of about 3.5 melt and a diameter of about 20 mm, an applicator is used, which is transparent in the spectral range of 625-700 nm, has a base in the form of a film in the shape of a circle having a diameter of 28 mm, the film being made from regenerated cellulose, and with a sensitizing layer containing a carrier of terpolymers. N-vinylpyrrolidone, an acrylic acid amide, and ethyl ester of acrylic acid with a ratio of the monomer links 25:50:25 wt. % and a molecular weight of 320 000 Daltons, in which 5-ALA in an amount of 30 mg/cm$^2$ is dissolved. The applicator was pressed against the surface of the pathological area. After 3 hours, the pathological area was irradiated through the applicator by laser radiation with a wavelength of 633 nm, the intensity of fluorescence in the spectral range of 635-700 nm was monitored and the concentration of the sensitizer evaluated on the basis of that measurement. After the therapeutic concentration of the sensitizer was reached, the pathological area was irradiated through the applicator by laser radiation with a wavelength of 628 nm, power density of 100 mW/cm$^2$ and dose density of 60 J/cm$^2$. A repeated diagnostic fluorescent study of the pathological area one day after the therapeutic irradiation indicated necrosis of the tumoral tissue over virtually the whole area of the irradiated tumor except for one small portion with retained tumoral tissue, in which, due to the sensitizing action of the applicator, a high concentration of the sensitizer was maintained, which was confirmed by the results of a fluorescent study. Repeated irradiation of the detected portion was carried out through the applicator by therapeutic laser radiation with a wavelength of 628 nm, power density of 100 mW/cm$^2$ and dose density of 20 J/cm$^2$. After two days a dry crust was formed over the whole surface of the pathological area. Data on pathomorphological studies of the tissues at the pathological area showed necrosis of the tumoral tissues at a depth to 4 mm. Studies of tissues of the area after PDT showed complete regression of the tumor.

Example 2

In order to carry out sensitization of a pathological area with basal cell skin carcinoma having a thickness of about 1.5 mm and a diameter of about 10 mm, an applicator was used, which was transparent in the spectral ranges of 625-700 nm and 510-540 nm, with a base in the form of a film of regenerated cellulose and with a sensitizing layer containing a carrier in the form of a film in the shape of a circle having a diameter of 18 mm, the film being made of terpolymer N-vinylpyrrolidone, an acrylic acid amide, and ethyl ester of acrylic acid with a ratio of the monomer links 25:55:20 wt.% and a molecular weight of 300 000 Daltons, in which 5-ALA in an amount of 20 mg/cm$^2$ is dissolved. The applicator was pressed against the surface of the pathological area. After 3 hours, the pathological area was irradiated through the applicator by laser radiation with a wavelength of 532 nm, the intensity of fluorescence in the spectral range of 635-700 nm was monitored and the concentration of the sensitizer evaluated on the basis of that measurement. After the therapeutic concentration of the sensitizer was reached, the pathological area was irradiated through the applicator by laser radiation with a wavelength of 628 nm, power density of 100 mW/cm$^2$ and dose density of 60 J/cm$^2$. Data on pathomorphological studies of the tissues at the pathological area showed complete regression of the tumor, necrosis of the tumoral tissues at a depth to 1.5 mm.

Example 3

In order to carry out sensitization of a pathological area with basal cell skin carcinoma of the nose having a thickness of about 1.5 mm and a diameter of about 10 mm, an applicator was used, which was transparent in the spectral range of 625-700 nm, with a base in the form of a film in the shape of a circle having a diameter of 18 mm, the film being made from regenerated cellulose, and with a sensitizing layer containing a carrier of terpolymer N-vinylpyrrolidone, an acrylic acid amide, and ethyl ester of acrylic acid with a ratio of the monomer links 33:38:29 wt. % and a molecular weight of 970 000 Daltons, in which 5-ALA in an amount of 30 mg/cm$^2$ was dissolved. The applicator was pressed against the surface of the pathological area. After 4 hours, the pathological area was irradiated through the applicator by laser radiation with a wavelength of 633 nm, the intensity of fluorescence in the spectral range of 635-700 nm was monitored and the concentration of the sensitizer evaluated on the basis of that measurement. After the therapeutic concentration of the sensitizer was reached, the pathological area was irradiated through the applicator by laser radiation with a wavelength of 628 nm, power density of 100 mW/cm$^2$ and dose density of 60 J/cm$^2$. A repeated diagnostic fluorescent study of the pathological area one day after the therapeutic irradiation indicated necrosis of the tumoral tissue over virtually the whole area of the irradiated tumor except for one small portion with retained tumoral tissue, in which, due to the sensitizing action of the applicator, a high concentration of the sensitizer was maintained, which was confirmed by the results of a fluorescent study. A repeated irradiation of the detected portion was carried out through the applicator by therapeutic laser radiation with a wavelength of 628 nm, power density of 100 mW/cm$^2$ and dose density of 20 J/cm$^2$. A dry crust was formed over the whole surface of the pathological area two days after the irradiation. Data on pathomorphological studies of the tissues at the pathological area showed necrosis of the tumoral tissues at a depth to 2 mm. Studies of tissues at the area after PDT showed complete regression of the tumor.

Example 4

In order to carry out sensitization of a pathological area with skin metastasis of mammary gland carcinoma having a thickness of about 3.5 mm and a diameter of about 10 mm, an applicator was used, which was transparent in the spectral ranges of 625-700 nm and 390-460 nm, with a base in the form of a film of polyethylene terephthalate and with a sensitizing layer containing a carrier in the form of a film in the shape of a circle having a diameter of 50 mm, the film being made from terpolymer N-vinylpyrrolidone, an acrylic acid amide, and ethyl ester of acrylic acid with a ratio of the monomer links 21:59:20 wt. % and a molecular weight of 30 000 Daltons, in which 5-ALA in an amount of 30 mg/cm$^2$ was dissolved. The applicator was pressed against the surface of the pathological area. After 4 hours, the pathological area was irradiated through the applicator by laser radiation with a wavelength of 442 nm, the intensity of fluorescence in the spectral range of 635-700 nm was monitored and the concentration of the sensitizer evaluated on the basis of that measurement. After the therapeutic concentration was reached, the pathological area was irradiated through the applicator by laser radiation with a wavelength of 628 nm, power density of 100 mW/cm$^2$ and dose density of 120 J/cm$^2$. Data on pathomorphological studies of the tissues at the pathological area showed necrosis of the tumoral tissues at a depth to 4 mm.

Example 5

In order to carry out sensitization of a pathological area with recurring basal cell carcinoma having a depth of about 1.5 mm and a diameter of about 10 mm, an applicator was used, which was transparent in the spectral range of 570-700 nm, with a base in the form of a film of polyamide and with a sensitizing layer containing a carrier in the form of a film in the shape of a circle having a diameter of 20 mm, the film being made of terpolymer N-vinylpyrrolidone, an acrylic acid amide, and ethyl ester of acrylic acid with a ratio of the monomer links 21:59:20 wt. % and a molecular weight of 22 000 Daltons, in which 5-ALA in an amount of 30 mg/cm$^2$ was dissolved. The applicator was pressed against the surface of the pathological area. After 4 hours, the pathological area was irradiated through the applicator by laser radiation with a wavelength of 578 nm, the intensity of fluorescence in the spectral range of 635-700 nm was monitored and the concentration of the sensitizer evaluated on the basis of that measurement. After the therapeutic concentration of the sensitizer was reached, the pathological area was irradiated through the applicator by laser radiation with a wavelength of 630 nm, power density of 100 mW/cm$^2$ and dose density of 120 J/cm$^2$. Data on pathomorphological studies of the tissues at the pathological area showed necrosis of the tumoral tissues at a depth to 2.5 mm.

The transparency of the applicator and the possibility of irradiation through it make it possible in the process of sensitization to, if necessary, carry out additional therapeutic irradiation in those cases when the main irradiation has not resulted in a complete destruction of the tumor, for example, because of insufficient concentration of the sensitizer at the moment of the beginning of the therapeutic irradiation, specificities of the pathological area or an insufficient dose of irradiation, and zones of tumoral cells remain in which the sensitizer continues to accumulate due to the inflow of 5-aminolevulinic acid from the proposed applicator. Moreover, irradiation at the beginning of the process of sensitization may result in an additional accumulation of the sensitizer in the tumoral tissues [Patent RF No. 2146159, priority from 11 Apr. 1996, IPC A 61 N 5/06]. This provides the possibility of enhancing the efficacy of the PDT. Wherewith, since an applicator fixed to the area prior to the start of the action is used during the whole process of action on the pathological area, both the risk of traumatic damage to or infection of the area and the expenditure of 5-aminolevulinic acid are reduced.

The proposed method for photodynamic therapy and the applicator for implementation thereof may be used during treatment of both surface tumors (for example, basal cell skin carcinoma) and benign diseases of skin integument (in particular, psoriasis and others).

What is claimed is:

1. A method for photodynamic therapy of an area, site or zone of psoriasis, basal cell carcinoma and skin metastasis of mammary gland carcinoma, the method comprising:
   sensitizing a surface of the pathological area, site or zone by superimposing an applicator comprising 5-aminolevulinic acid, and
   irradiating the sensitized area, site or zone with therapeutic optical radiation in the spectral range of 625-700 nm, characterized in that the applicator through which irradiation passes comprises:
   a base of a bioinert material and
   a sensitizing layer including a carrier and 5-aminolevulinic acid dissolved or dispersed in the carrier,
   further characterized in that
   the base is made in the form of a bioinert polymer, transparent in the spectral range of at least 625-700 nm, and
   the carrier is made in the form of a film layer of biocompatible hydrophilic copolymers comprising N-vinylpyrrolidone, acrylic acid amide, and ethyl ester of acrylic acid with
   a ratio of the monomeric links respectively (20-35):(35-60):(20-30) wt. % and
   a molecular weight of from 20,000 to 1,000,000 Daltons.

2. The method of claim 1, characterized in that an applicator is used which is also transparent in at least one of the spectral ranges 390-460 nm, 510-540 nm or 570-590 nm, while monitoring the intensity of fluorescence of the tissues of the pathological area is carried out by irradiation in one of said ranges and measurement of the intensity of fluorescence in the range of 635-700 nm through said applicator.

3. The method of claim 1, characterized in that the bioinert polymer is also transparent in at least one of the spectral ranges of 390-460 nm, 510-540 nm or 570-590 nm.

4. The method of claim 1, characterized in that regenerated cellulose, polyethylene terephthalate or a polyamide is used as the bioinert polymer.

5. The method of claim 2, characterized in that regenerated cellulose, polyethylene terephthalate or a polyamide is used as the bioinert polymer.

* * * * *